United States Patent [19]

Klipa et al.

[11] Patent Number: 5,486,638

[45] Date of Patent: Jan. 23, 1996

[54] PROCESS FOR THE PREPARATION OF 1-HALO-3-TRIALKYSILANYL-BENZENE DERIVATIVES

[75] Inventors: Dennis K. Klipa; Robert T. Keaten, both of Midland, Mich.

[73] Assignee: Marion Merrell Dow Inc., Cincinnati, Ohio

[21] Appl. No.: 336,142

[22] Filed: Nov. 8, 1994

[51] Int. Cl.$^6$ ................................................ C07F 7/08
[52] U.S. Cl. ................................................ 556/480
[58] Field of Search ................................. 586/400

[56] References Cited

U.S. PATENT DOCUMENTS

| | | |
|---|---|---|
| 3,080,324 | 3/1963 | Richards et al. |
| 3,347,897 | 10/1967 | Webster. |
| 4,116,993 | 9/1978 | Bluestein et al. ........................ 556/480 |

FOREIGN PATENT DOCUMENTS

| | | |
|---|---|---|
| 0409676 | 6/1989 | European Pat. Off. . |
| 0403713 | 12/1990 | European Pat. Off. . |

OTHER PUBLICATIONS

Ramsden, Hugh E. et al., J. Org. Chem., vol. 22, pp. 1202–1206 (1957).

Chen, J. G. and Tamborski, J. Organometallic Chemistry, vol. 251, pp. 149–158 (1983).

Odabashyan, G. V. et al., Chemical Abstracts vol. 76, p. 478, 153843W, (1972).

*Primary Examiner*—Paul F. Shaver
*Attorney, Agent, or Firm*—Nelsen L. Lentz

[57] ABSTRACT

The present invention relates to a novel process for preparing 1-halo-3-trialkylsilanyl-benzenes from 1,3-dihalo-benzenes which are useful intermediates in the preparation of 1-(3-trialkylsilylphenyl)-2,2,2-trifluoromethyl ethanones which are useful for the treatment of Alzheimer's disease and senile dementia.

15 Claims, No Drawings

5,486,638

PROCESS FOR THE PREPARATION OF 1-HALO-3-TRIALKYSILANYL-BENZENE DERIVATIVES

BACKGROUND OF THE INVENTION

The present invention relates to a novel process for preparing 1-halo-3-trialkylsilanyl-benzenes which are useful intermediates in the preparation of 1-(3-trialkylsilylphenyl)- 2,2,2-trifluoromethyl ethanones which are useful for the treatment of Alzheimer's disease and senile dementia as disclosed by Schirlin, et al. in European Patent Application Publication No. 0 409 676, published Jan. 23, 1991.

SUMMARY OF THE INVENTION

The present invention provides a novel process for the preparation of a compound of the formula (I):

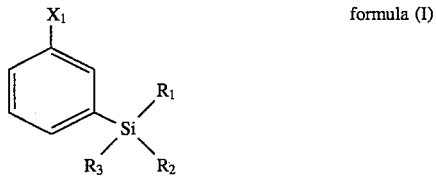

formula (I)

wherein $X_1$ is Cl, Br or I; and $R_1$, $R_2$ and $R_3$ are each independently $C_1$–$C_4$ alkyl, comprising adding a suitable ether to a mixture of $ClSiR_1R_2R_3$, magnesium, a suitable aromatic solvent and a compound of the formula (II):

formula (II)

wherein $X_1$ and $X_2$ are each independently Cl, Br or I and $R_1$, $R_2$ and $R_3$ are defined as above; provided $X_2$ is other than Br or Cl when $X_1$ is I; and further provided $X_2$ is other than Cl when $X_1$ is Br.

DETAILED DESCRIPTION OF THE INVENTION

As used herein the term "$C_1$–$C_4$ alkyl" refers to a saturated straight or branched chain hydrocarbon radical of one to four carbon atoms. Included within the scope of this term are methyl, ethyl, n-propyl, isopropyl, n-butyl, isobutyl and the like. As used herein the terms "halo", "halogen" or "halide" refer to a chlorine, bromine or iodine atom.

The process of the present invention is described in Scheme I. All the substituents, unless otherwise indicated, are previously defined. The reagents and starting materials are readily available to one of ordinary skill in the art.

Scheme I

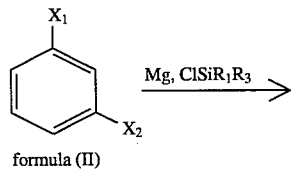

formula (II)

-continued
Scheme I

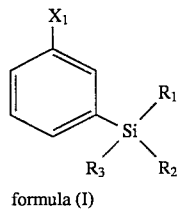

formula (I)

In Scheme I, a compound of formula (I) is prepared from a dihalo compound of formula (II) under the following conditions.

The dihalo compound of formula (II) is combined with magnesium, $ClSiR_1R_2R_3$ and a suitable aromatic solvent under an inert atmosphere, such as nitrogen. It is preferred that all reagents and starting materials be essentially anhydrous. Examples of a dihalo compound of formula (II) are 1,3-dibromobenzene, 1,3-dichlorobenzene, 1-chloro-3-bromobenzene, 1,3-diiodobenzene, 1-chloro-3-iodobenzene and 1-bromo-3-iodobenzene, with the preferred dihalo compound of formula (II) being 1,3-dibromobenzene. The total number of equivalents of magnesium employed in the process of Scheme I relative to the dihalo compound of formula (II) is from about 0.9 eq to about 1.1 eq, with about 1 eq being preferred. In addition, magnesium suitable for Grignard reactions is preferred, such as magnesium powder, magnesium granules, magnesium ribbon, magnesium turnings and the like. Magnesium turnings are most preferred. The reaction vessel is fitted with an agitator, such as a retreat curve agitator. The agitator is set at a speed sufficient for good mixing. The total number of equivalents of $ClSiR_1R_2R_3$ employed in the process of Scheme I relative to the dihalo compound of formula (II) is from about 0.8 eq to about 1.2 eq, with about 1.1 eq being preferred. Examples of $ClSiR_1R_2R_3$ are chlorotriethylsilane, chloro-tri-n-propylsilane, chloro-tri-n-butylsilane, chlorodimethylethylsilane, chlorodimethylisopropylsilane, chlorotrimethylsilane and the like. Chlorotrimethylsilane is the preferred $ClSiR_1R_2R_3$. The mass ratio of suitable aromatic solvent to dihalo compound of formula (II) employed in the process of Scheme I is from about 3 to about 10, with about 4.6 being preferred. For example, as described in Table 1, batch #2, 810 lb of toluene are utilized with 176 lb of 1,3-dibromobenzene resulting in a mass ratio of 4.6 (810 lb/176 lb). Examples of a suitable aromatic solvent are benzene, ethylbenzene, xylene, diethylbenzene, toluene and the like. The preferred suitable aromatic solvent is toluene. The above mixture is heated at a temperature of from about 20° C. to about 80° C. The preferred temperature of the mixture is about 50° C. When the temperature of the mixture begins to fall, the addition of a suitable ether is initiated. Examples of a suitable ether are diethyl ether, tetrahydropyran, tetrahydrofuran, and the like. The preferred suitable ethers are tetrahydropyran and tetrahydrofuran, with tetrahydrofuran being most preferred. The total number of equivalents of suitable ether employed in the process of Scheme I relative to the dihalo compound of formula (II) is from about 1.8 eq to about 4 eq, with about 2.5 eq of suitable ether being preferred. It is preferred that from about 2% to about 15% of the total amount of the suitable ether be added to the mixture in one portion initially, with about 10% of the total amount of the suitable ether being the preferred initial amount added to the mixture. The remaining portion of the total amount of the suitable ether is then added at a rate of from about 0.15 eq/hour to about 2 eq/hour, with about 0.7 eq/hour to about 1.2 eq/hour being preferred and 1.13 eq/hour being the most preferred rate of addition of the suitable ether. The controlled rate of addition of the remaining portion of the total amount of the suitable ether allows the temperature of the reaction to be controlled and essentially maintained at the mixture temperature, such as the preferred temperature of 50° C. It is preferred that the temperature of the process of Scheme I be maintained at about 50° C. during addition of the suitable ether. After addition of the total amount of suitable ether is complete, the reaction is allowed to stir for about 10 hours to about 15 hours at a temperature of from about 20° C. to about 70° C. with about 50° C. being the preferred temperature. The slurry is then cautiously added to water which is at a temperature of from about 5° C. to about 50° C., with stirring. The compound of formula (I) is then isolated and purified by techniques well known in the art, such as extractive methods, distillation, chromatography and the like. For example, the mixture is then stirred for about 10 minutes to about 1 hour. The phases are then separated and the organic phase is optionally subjected to a second water wash. The organic phase is then dried with a suitable drying agent, such as anhydrous magnesium sulfate, filtered and concentrated under vacuum to provide the compound of formula (I) which can be further purified by techniques well known in the art such as chromatography and/or vacuum distillation.

The following examples present typical syntheses as described in Scheme I. These examples are understood to be illustrative only and are not intended to limit the scope of the present invention in any way. As used herein, the following terms have the indicated meanings: "g" refers to grams; "mmol" refers to millimoles; "L" refers to liters; "ml" refers to milliliters; "bp" refers to boiling point; "mp" refers to melting point; "°C." refers to degrees Celsius; "mm Hg" refers to millimeters of mercury; "μL" refers to microliters; "μg" refers to micrograms; "μM" refers to micromolar; "eq" refers to equivalents; "min" refers to minutes; "rpm" refers to revolutions per minute; and "lb" refers to pounds.

EXAMPLE 1

Small scale preparation of
1-bromo-3-trimethylsilanyl-benzene.

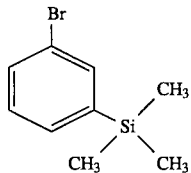

Scheme Z; A 500 mL round-bottomed, 3 necked, fluted flask with a thermowell is fitted with an addition funnel, mechanical stirrer, reflux condenser and thermocouple recorder. The atmosphere is flushed with nitrogen. Magnesium (4.84 g, 0.199 mole), chlorotrimethylsilane (45.9 g, 0.422 mole), toluene (214 g) and 1,3-dibromobenzene (46.5 g, 0.197 mole) are then added. The mixture is heated to 50° C. with a heat gun and then allowed to slowly cool. When the temperature starts to fall, tetrahydrofuran (38.1 g) is added. The temperature continues to fall to 42° C. where it stabilizes and then begins to rise. The temperature is controlled at 50°±2° C. while the remaining tetrahydrofuran (342.9 g) is added dropwise (1 drop every 5 to 8 seconds) over a 2 hour period. When about 60–70% of the tetrahydrofuran has been added the exotherm subsides and a fluffy solid forms. The remainder of the tetrahydrofuran is added rapidly without evidence of an exotherm. The mixture is then allowed to cool to room temperature overnight. The slurry is vacuum transferred to a one liter flask containing water heated to 50° C. producing a temperature increase. The mixture is stirred for 10 minutes and the phases are separated (mixture temperature is 45° C. when separated). The organic phase is washed with water (50 mL), dried over anhydrous magnesium sulfate/sodium sulfate, filtered, concentrated under vacuum and distilled through a 40 theoretical plate concentric tube distillation column at 15 mm Hg. The title compound is then collected at a temperature of from 94° C. to 105° C. to provide a colorless oil (32.7 g, 76.8%).

Reverse-phase HPLC (high performance liquid chromatography) analysis of the title compound can be performed utilizing a Hitachi Model L-6200 gradient pump, a Perkin-Elmer Diode Array 235 Detector, a Spectra-Physics Model 4270 integrator, a Hitachi Model AS-2000 autosampler, and a Rheodyne Model 7125 injector equipped with a 20 μL sample loop and a 4.0×80 mm Zorbax ODS (5 μm particles) column. The detector is set at 255 nm, the mobile phase is 90:10 acetonitrile/water and the flow rate is set at 2 mL/min resulting in a retention time ($R_t$) for the title compound of about 0.92 to 0.95 minutes.

Preparative LC (liquid chromatography) of the title compound can be performed utilizing a Gilson Model 305 pump equipped with a Gilson Manometric Module Model 805, a Linear Model UV-106 (254nm) detector, a Sargent-Welch Model SRG-2 chart recorder, and a Rheodyne 7125 injector equipped with a 1.0 mL sample loop and an Alltech 22.5× 250 mm Econosphere $C_{18}$ (10 μm particles) column. The crude material is dissolved in acetonitrile prior to injection. The detector is set at 254 nm, the mobile phase can be 90:10 or 85:15 acetonitrile/water and the flow rate is set at 15 mL/min resulting in an $R_t$ range for the title compound of about 8.5 to 11 minutes.

Gas chromatographic analysis of the title compound can be performed utilizing a Hewlett Packard 5890A Gas Chromatograph, a Hewlett Packard 7573A Autosampler fitted with a 10 μL syringe, a Hewlett Packard 7673 Autosampler Tray, a flame ionization detector, a PE-Nelson AccessChrom Rev. 1.9 with model 941 A/D data system, a Supelco SPB-1 30 m×0.32 mm ID column with 1μ film thickness (cut from a 60 m column) and helium as the carrier gas. The conditions used are a 10 psi column head pressure, a 105 mL/min split flow, a 1.8 mL/min column flow, 20 mL/min detector make up (nitrogen), 20 mL/min detector hydrogen flow, 300 mL/min detector air flow, detector range=2, injector temperature of 275° C. and a detector temperature of 300° C. The temperature gradient program used has an initial temperature of 60° C. that increases to 130° C. at a rate of about 16° C./min, it is then held at 130° C. for 12 min, and finally increased to 320° C. at a rate of about 22° C. /min at which time the run is terminated. The retention time is approximately 16 min for 1-bromo-3-trimethytsilanyl-benzene.

Example 1a provides the general procedure followed for 10 separate batches for the large scale preparation of 1-bromo- 3-trimethylsilanyl-benzene. Following Example 1a, Table 1 provides the individual amounts of reagents and starting materials utilized and the results obtained for each of the 10 batches.

Example 1a

Large scale preparation of
1-Bromo-3-trimethylsilanyl-benzene.

Scheme I, ; Magnesium turnings (18.25 lb) are loaded into a 200 gallon glass-lined reactor fitted with a retreat curve agitator. The reactor is sealed, pressure tested and purged with nitrogen. 1,3-dibromobenzene (176 lb) is then vacuum loaded into the reactor followed by vacuum loading of toluene (806.6 lb). The agitator is set to 130 rpm in order to obtain good mixing. Chlorotrimethylsilane (180 lb) is then loaded into the reactor by adding nitrogen pressure to the cylinder of chlorotrimethylsilane and opening the cylinder to the reactor headspace. After loading the chlorotrimethylsilane, the transfer line is blown clear with nitrogen. The temperature control system of the reactor is set to maintain an internal reactor temperature of 50° C. When the internal temperature and jacket temperature of the reactor stabilize at 50° C., tetrahydrofuran (14 lb) is pumped into the reactor headspace. The temperature of the reactor is monitored to determine when the reaction (exothermic) starts. The reaction is determined to have started when the difference between the internal temperature of the reactor and the jacket temperature is greater than 5°–10° C. After the reaction starts, tetrahydrofuran (130 lb) is pumped into the reactor at a rate of about 0.7 eq/hour to about 1.2 eq/hour. After addition of the tetrahydrofuran is complete, the reactor contents are agitated for an additional 10–15 hours at 50° C.

The contents of the reactor are then transferred to a 300 gallon glass-lined reactor fitted with a pitched blade agitator and containing water (about 100 gallons at 5°–10° C. ). Toluene (about 20 lb) is vacuum loaded into the original 200 gallon reactor and is used to flush the transfer line between the 200 gallon and 300 gallon reactors. The 300 gallon reactor is agitated for about one hour, agitation is then stopped and the contents are allowed to settle for about 30–60 minutes. The aqueous phase is then drained out of the 300 gallon reactor and water (about 25 gallons) is again added, followed by agitation for about 30 minutes. The agitation is then stopped, the contents are allowed to settle for about 30–90 minutes and the aqueous layer is drained out of the 300 gallon reactor. The organic phase is then drained to 55 gallon drums.

The 300 gallon reactor is then pressure tested, purged with nitrogen and about 1600–2000 lb of the above organic solution from the 55 gallon drums is vacuum loaded into the reactor. The agitator is set at about 100 rpm and the jacket system set to hold the jacket temperature at 10°–20° C. above the internal temperature to begin distillation of the volatiles into a distillate receiver. As the level in the reactor decreases, additional organic solution from the 55 gallon drums is loaded until 5 batches have been loaded into the reactor. The distillation is continued until the internal temperature of the reactor reaches 68°–72° C. The jacket temperature is then set to about 25° C. and the vacuum is broken with nitrogen. When the internal temperature of the reactor is less then about 35° C., the manway is opened and diatomaceous earth (about 20 lb) and magnesium sulfate (about 20 lb) are loaded into the reactor through the manway. The manway is then closed and the reactor is pressure tested and purged with nitrogen. The contents of the reactor are then drained into 55 gallon drums through a Nutsche filter (prepared by placing a new filter cloth in the bottom) to provide the title compound.

TABLE 1

Summary of Reaction Conditions and % Yield of 1-Bromo-3-trimethylsilanyl-benzene for Ten Individual Batches Following the Procedure Described in Example 1 for each Individual Batch in an Analogous Manner.

|  | #1 | #2 | #3 | #4 | #5 | #6 | #7 | #8 | #9 | #10 | total |
|---|---|---|---|---|---|---|---|---|---|---|---|
| Magnesium (lb) | 18.25 | 18.25 | 18.25 | 18.25 | 18.25 | 18.25 | 18.3 | 18.5 | 18.3 | 17.5 | 182 |
| 1,3-Dibromobenzene (lb) | 176 | 176 | 176 | 176 | 176 | 176 | 176 | 176 | 176.3 | 168.9 | 1753 |
| Toluene (lb) | 806.6 | 810 | 811 | 812 | 810 | 811 | 810 | 810 | 814 | 780 | 8075 |
| Chlorotrimethylsilane (lb) | 176 | 180 | 178 | 159 | 176 | 171 | 172 | 215 | 177 | 138 | 1742 |
| Initial THF (lb) | 28 | 14 | 14 | 14 | 14 | 14 | 14 | 14 | 14.1 | 13.3 | 153 |
| Final THF (lb) | 116 | 130 | 130 | 130 | 130 | 130.1 | 130 | 130 | 120 | 125 | 1271 |
| Total THF (lb) | 144 | 144 | 144 | 144 | 144 | 144.1 | 144 | 144 | 144.1 | 138.3 | 1434.5 |
| Time for final THF addition (min) | 140 | 180 | 140 | 145 | 145 | 135 | 160 | 194 | 210 | 215 |  |
| Quench water (gal) | 100 | 100 | 100 | 100 | 100 | 100 | 100 | 100 | 100 | 100 | 1000 |
| Toluene flush (lb) | 21.5 | 20 | 20 | 20 | 20 | 20 | 20 | 28 | 20 | 21 | 211 |
| Water wash (gal) | 25 | 25 | 25 | 25 | 25 | 25 | 25 | 25 | 25 | 25 | 250 |
| Agitator speed (rpm) | 130.4 | 130.8 | 130 | 110 | 110 | 135 | 133 | 135 | 132.5 | 127 |  |
| % yield of 1-Bromo-3-trimethylsilanyl-benzene | 64.58 | 68.78 | 63.93 | 64.90 | 63.53 | 64.39 | 64.35 | 63.40 | 66.20 | 66.04 | 65.0 |

Example 2

Preparation of 1-Chloro-3-trimethylsilanyl-benzene.

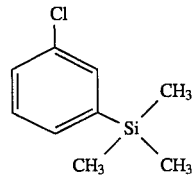

Scheme I; 1-Chloro-3-trimethylsilanyl-benzene is prepared in a manner analogous to the procedure described in examples 1 and 1a utilizing chlorotrimethylsilane and 1-chloro-3-bromobenzene as the dihalo compound of formula (II).

Example 3

Preparation of 1-Bromo-3-trimethylsilanyl-benzene.

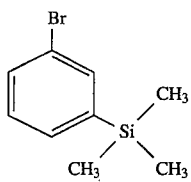

Scheme I; 1-Bromo-3-trimethylsilanyl-benzene is prepared in a manner analogous to the procedure described in examples 1 and 1a utilizing chlorotrimethylsilane and 1-bromo- 3-iodobenzene as the dihalo compound of formula (II).

Example 4

Preparation of 1-Chloro-3-trimethylsilanyl-benzene.

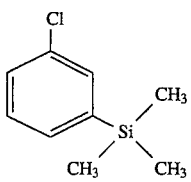

Scheme I; 1-Chloro-3-trimethylsilanyl-benzene is prepared in a manner analogous to the procedure described in examples 1 and 1a utilizing chlorotrimethylsilane and 1-chloro- 3-iodobenzene as the dihalo compound of formula (II).

Example 5

Preparation of 1-Iodo-3-trimethylsilanyl-benzene.

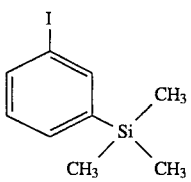

Scheme I; 1-Iodo-3-trimethylsilanyl-benzene is prepared in a manner analogous to the procedure described in examples 1 and 1a utilizing chlorotrimethylsilane and 1,3-diiodobenzene as the dihalo compound of formula (II).

Example 6

Preparation of 1-Bromo-3-triethylsilanyl-benzene.

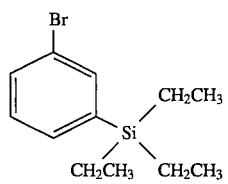

Scheme I; 1-Bromo-3-triethylsilanyl-benzene is prepared in a manner analogous to the procedure described in examples 1 and 1a utilizing 1,3-dibromobenzene and chlorotriethylsilane as the $ClSiR_1R_2R_3$ compound.

Example 7

Preparation of 1-Bromo-3-tri-n-propylsilanyl-benzene.

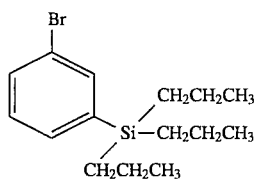

Scheme I; 1-Bromo-3-tri-n-propylsilanyl-benzene is prepared in a manner analogous to the procedure described in examples 1 and 1a utilizing 1,3-dibromobenzene and chlorotri-n-propylsilane as the $ClSiR_1R_2R_3$ compound.

Example 8

Preparation of 1-Bromo-3-dimethylethylsilanyl-benzene.

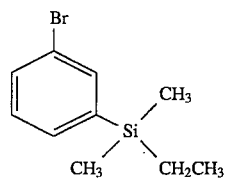

Scheme I; 1-Bromo-3-dimethylethylsilanyl-benzene is prepared in a manner analogous to the procedure described in examples 1 and 1a utilizing 1,3-dibromobenzene and chlorodimethylethylsilane as the $ClSiR_1R_2R_3$ compound.

Example 9

Preparation of 1-Bromo-3-dimethylisopropylsilanyl-benzene.

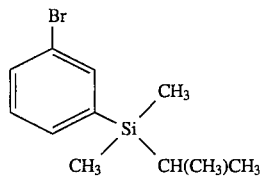

Scheme I; 1-Bromo-3-dimethylisopropylsilanyl-benzene is prepared in a manner analogous to the procedure described in examples 1 and 1a utilizing 1,3-dibromobenzene and chlorodimethylisopropylsilane as the $ClSiR_1R_2R_3$ compound.

Example 10

Preparation of 1-Bromo-3-tri-n-butylsilanyl-benzene.

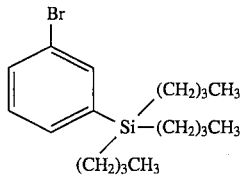

Scheme I; 1-Bromo-3-tri-n-butylsilanyl-benzene is prepared in a manner analogous to the procedure described in examples 1 and 1a utilizing 1,3-dibromobenzene and chloro-tri-n-butylsilane as the $ClSiR_1R_2R_3$ compound.

What is claimed is:

1. A process for the preparation of a compound of the formula:

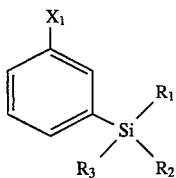

wherein $X_1$ is Cl Br or I; and $R_1$, $R_2$ and $R_3$ are each independently $C_1$–$C_4$ alkyl, comprising adding a suitable ether to a mixture of $ClSiR_1R_2R_3$, magnesium, a suitable aromatic solvent and a compound of the formula:

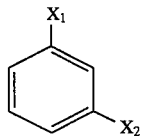

wherein $X_1$ and $X_2$ are each independently Cl Br or I and $R_1$, $R_2$ and $R_3$ are defined as above; provided $X_2$ is other than Br or Cl when $X_1$ is I; and further provided $X_2$ is other than Cl when $X_1$ is Br.

2. A process according to claim 1 wherein a total amount of about 2.5 equivalents of the suitable ether is added to the mixture.

3. A process according to claim 2 wherein about 10% of the total amount of the suitable ether is added to the mixture in one portion and the remaining 90% of the total amount of the suitable ether is then added at a rate of from about 0.15 eq/hour to about 2 eq/hour.

4. A process according to claim 2 wherein about 10% of the total amount of the suitable ether is added to the mixture in one portion and the remaining 90% of the total amount of the suitable ether is then added at a rate of from about 0.7 eq/hour to about 1.2 eq/hour.

5. A process according to claim 2 wherein about 10% of the total amount of the suitable ether is added to the mixture in one portion and the remaining 90% of the total amount of the suitable ether is then added at a rate of about 1.13 eq/hour.

6. A process as in one of claims 3–5 wherein the mixture is heated to a temperature of from about 20° C. to about 80° C. just prior to addition of the suitable ether.

7. A process as in one of claims 3–5 wherein the mixture is heated to a temperature of about 50° C. just prior to addition of the suitable ether.

8. A process according to claim 7 wherein the total number of equivalents of magnesium is from about 0.9 eq to about 1.1 eq.

9. A process according to claim 7 wherein the total number of equivalents of magnesium is about 1 eq.

10. A process according to claim 9 wherein the suitable ether is tetrahydrofuran.

11. A process according to claim 10 wherein the suitable aromatic solvent is toluene.

12. A process according to claim 11 wherein $X_1$ and $X_2$ are Br.

13. A process according to claim 12 wherein $R_1$, $R_2$ and $R_3$ are each methyl.

14. A process according to claim 13 further comprising stirring the reaction at a temperature of from about 20° C. to about 70° C. for about 10 hours to 15 hours after addition of the total amount of the suitable ether is complete.

15. A process according to claim 14 wherein the reaction is stirred at a temperature of about 50° C. after addition of the total amount of the suitable ether is complete.

* * * * *

UNITED STATES PATENT AND TRADEMARK OFFICE
CERTIFICATE OF CORRECTION

PATENT NO.   : 5,486,638
DATED        : January 23, 1996
INVENTOR(S)  : Dennis K. Klipa, et al.

It is certified that error appears in the above-identified patent and that said Letters Patent is hereby corrected as shown below:

At Column 3, line 54, the patent reads "Scheme Z" and should read --Scheme I.

Signed and Sealed this

Twenty-fourth Day of September, 1996

Attest:

BRUCE LEHMAN

Attesting Officer        Commissioner of Patents and Trademarks